United States Patent [19]

Janese

[11] Patent Number: 4,904,237
[45] Date of Patent: Feb. 27, 1990

[54] APPARATUS FOR THE EXCHANGE OF CEREBROSPINAL FLUID AND A METHOD OF TREATING BRAIN AND SPINAL CORD INJURIES

[76] Inventor: Woodrow W. Janese, Janus Medical Instruments, 2806 N. Navaro, Suite M, Victoria, Tex. 77901

[21] Appl. No.: 194,363

[22] Filed: May 16, 1988

[51] Int. Cl.⁴ .............................................. A61M 1/00
[52] U.S. Cl. ........................................ 604/28; 604/31; 604/65; 604/280
[58] Field of Search .................................. 604/27-28, 604/30-31, 32, 51-53, 65-67, 158, 246, 280

[56] References Cited

U.S. PATENT DOCUMENTS

| | | | |
|---|---|---|---|
| 3,680,562 | 8/1972 | Wittes et al. | 604/168 X |
| 4,686,085 | 8/1987 | Osterholm | 604/23 X |
| 4,756,706 | 7/1988 | Kerns et al. | 128/DIG. 13 X |

OTHER PUBLICATIONS

Geigi, "Scientific Tables", ©1970 CIBA-Geigi, pp. 635-640.
J. Neurosurg., D. Boullin, et al. 55:237-245 (1981).
Neurosurgery, T. Brott and T. Mandybur 19:891-895 (1986).
Neurosurgery, T. Doczi and F. Joo.
J. Neurosurg., T. Duff, G. Scott and J. Feilbach 64:292-297 (1986).
Neurosurgery, M. Grady, G. Cooper, N. Kassell and I. Logan 18:653-659 (1986).
J. Neurosurg., Y. Hands et al. 67:558-564 (1987).
Neurosurgery, Y. Kawakami and Y. Shimamura 20:8-14 (1987).
J. Neurosurg., A. Kaye et al. 60:927-934 (1984).
Marine Biological Laboratory, Review and update in Neurobiology for Neurosurgeons Nov. 14-25, 1986

Neurosurgery, T. Milhorat 20:15-20 (1987).
Neurosurgery, D. Pang, R. Slabassi and J. Horton 19:540-546 (1986).
Neurosurgery, T. Sasaki, et al. 19:177-184 (1986).
Neurosurgery, T. Terada et al. 18:415-418 (1986).
J. Neurosurg., E. Alexander, P. Black, T. Liszcak and Ann Zervas 63:949-958 (1985).
Neurosurgery, J. Alksne, P. Branson and M. Bailey 19:20-25 (1986).
J. Neurosurg., D. Boullin, et al. 50:231-236.
Neurosurgery, R. Wilkins 18:808-818 (1986).
Neurosurgery, H. Young, R. Kolbeck and H. Schmidek 19:502-506 (1986).
Bulletin American College of Surgeons, Ratcheson, R. A., 73:17-23 (1988).
Proceedings of the 36th Annual Meeting of the Congress of Neurological Surgeons, Dwan, P. S., et al. Chapter 29, pp. 604-617 (1988).

Primary Examiner—Francis Jaworski
Attorney, Agent, or Firm—Fulbright & Jaworski

[57] ABSTRACT

Disclosed is an apparatus and method for exchanging cerebrospinal fluid. The apparatus withdraws cerebrospinal fluid from the lumbar subarachnoid space, filters, cools, pH adjusts and performs diagnostic/monitoring functions on the fluid. It then returns purified and/or artificial spinal fluid to the subarachnoid space. The apparatus monitors fluid temperature and core body temperature. Furthermore, it detects increased subarachnoid hemorrhage or repeat subarachnoid hemorrhage. The apparatus is attached to an indwelling spinal cannula, and can continually exchange cerebrospinal fluid and monitor the patient. The apparatus can be completely controlled by computer with technician supervision for the treatment of patients needing purification of their spinal fluid.

17 Claims, 6 Drawing Sheets

APPARATUS FOR THE EXCHANGE OF CEREBROSPINAL FLUID AND A METHOD OF TREATING BRAIN AND SPINAL CORD INJURIES

FIELD OF THE INVENTION

The present invention relates generally to an apparatus and a method for exchanging cerebrospinal fluid. The apparatus treats disease states by filtration, cooling, adjusting hydrogen ion concentration and returning the cerebrospinal fluid or artificial cerebrospinal fluid to the spinal canal. This apparatus and procedure can be used in any vertebrate for the treatment of brain and spinal cord injuries. Furthermore, the apparatus and method can be used for monitoring the current status of a patient by monitoring the physical and chemical parameters of the cerebrospinal fluid.

BACKGROUND OF THE INVENTION

Approximately 20% of cardiac output is delivered primarily to the brain by two carotid arteries and two vertebral arteries. The blood is pumped by the heart at a mean systolic pressure of around 7.2 PSI and moves through a network of, progressively decreasing in caliber, elastic muscular conduits (arteries), ending in biologically active membranes (capillaries). Approximately 1% of the population has a weakening in the muscular layer at the branching point of certain cerebral arteries. The intraluminal pressure can expand the artery into an outpouching called an aneurysm at the site of the weakening. Furthermore, the pressure can become unduly elevated or a degenerative disease can attack and weaken the wall further. Under these conditions the aneurysms can rupture or tear.

Most of the weakened arteries are on the surface of the brain and directly in contact with the cerebrospinal fluid. The aneurysm rupture has a spectrum of presentations related to the opening of the high pressure arterial system (around 7 PSI) into the low pressure cerebrospinal fluid system (around 0.3 to 1.2 PSI). Although many times only a small amount of blood will leak into the cerebrospinal fluid and the arterial opening will close by clot formation, a huge 2 to 4 mm rent in the aneurysm can occur. This will allow a high pressure direct spout of blood, saturating the cerebrospinal fluid and/or eroding an opening into the adjacent brain, before the leak is sealed by clot formation. Mortality rate for this congenital disease is quite high. Thirty-four to forty percent die during the initial bleeding. Another 30–40% of the survivors die within the following four weeks. Thus, approximately 60% of individuals who develop a ruptured aneurysm die. Autopsy and incidence studies indicate that about 1% of the population have aneurysms. Currently, medical care is directed toward increasing the chance of survival after the aneurysm has ruptured and the individual reaches the hospital.

When blood enters the cerebrospinal fluid, vasospasm can occur and the arteries in contact with the cerebrospinal fluid decrease in calibre, resulting in decreased blood volume delivery to the capillary membrane and metabolizing tissue. The consequent decreased oxygen tension causes ischemia. Severe ischemia can cause cell death or necrosis and a permanent neurological function loss. The exact mechanism for initiation of vasospasm is unknown, but it is thought to involve blood borne factors which are liberated into the cerebrospinal fluid. The materials causing the vasospasm have not been identified though they have been found in blood and cerebrospinal fluid of subarachnoid hemorrhage. There is a positive correlation between the amount of subarachnoid blood and cerebral vasospasm observed.

After an initial subarachnoid hemorrhage, vasospasm seems to occur during the following time course: no spasm for the first through the fourth days, vasospasm after 5 to 22 days. A repeated subarachnoid hemorrhage, however, shortens the initial non-spasm period.

Currently the physician must balance the risks of treating a patient having subarachnoid bleeding. Although the optimal time to operate is between 7-14 days, vasospasm is likely to occur after only 4 days. Thus, by delaying surgery until 7-14 days after the initial bleed the surgical results improve and technically the surgery is easier, but more patients will die from vasospasm or repeat bleed.

Most attempts, to date, to treat or prevent intracranial arterial spasm have not been successful. The best predictor of vasospasm is the amount of blood within the basal subarachnoid cisterns four days after a spontaneous subarachnoid hemorrhage. This can be visualized directly or by a CT scan. The apparatus for cerebrospinal fluid exchange described in the present invention provides prophylaxis against symptomatic intra-cranial arterial spasm by removing blood and blood byproducts from the cerebrospinal fluid and by cooling the circulating cerebrospinal fluid to improve injured brain survival. Furthermore, the apparatus monitors normal cerebrospinal fluid pH, temperature, pressure and percent transmittance, providing immediate evidence of a repeat subarachnoid hemorrhage. This procedure will be much safer than current procedures which involve the removal of clotted blood and vasospastic effects from the subarachnoid cisterns. This has included mechanical removal by the surgeon of blood clots in the area of surgical exposure, drainage of the subarachnoid spaces, and ventricular cisternal irrigation for 7-14 days.

SUMMARY OF THE INVENTION

An object of the present invention is a fully computerized apparatus for the exchange of cerebrospinal fluid.

An additional object of the present invention is an apparatus for the filtration and treatment of cerebrospinal fluid.

A further object of the present invention is an apparatus for the cooling of cerebrospinal fluid for the treatment of disease.

Another object of the present invention is an automated computerized method for the diagnosis, treatment and monitoring of brain and spinal cord injury.

Thus in accomplishing the foregoing objects one aspect of the present invention is an apparatus for the exchange of cerebrospinal fluid comprising a collection means for obtaining cerebrospinal fluid. The collection means includes a cannula which punctures the spinal canal providing a conduit for a catheter which indwells in said canal. The outside surface of the catheter has a flange attached for retarding or preventing the leakage of cerebrospinal fluid from the subarachnoid compartment. The collection means is connected to a processing means for monitoring the exchange of the cerebrospinal fluid and the processing means is connected to a regulating means through an interface; said regulating means controlling the exchange of cerebrospinal fluid.

In one specific aspect of the present invention the catheter is a silicone elastomer with an outside diameter of about 1.22 mm and an internal diameter of about 0.97 mm. The processing means comprises a means for moving the cerebrospinal fluid from the subarachnoid compartment of the spinal canal through the processing means and back to the subarachnoid compartment of the spinal canal, a first container for holding the untreated cerebrospinal fluid, a filtration means for removing the particulate matter from the cerebrospinal fluid, a second container for storing the treated cerebrospinal fluid, a temperature regulating means for controlling the temperature of the cerebrospinal fluid and a means for monitoring the physical and chemical characteristics of the cerebrospinal fluid.

Another specific embodiment has a means for moving fluid including a peristaltic pump which is reversible, has a volume range of about 0.07 to 15 liters per hour, operates under a pressure of less than about 30 PSI and is attached to the regulating means through the interface. Additionally, a three port valve means is connected to the regulating means and is synchronously controlled with the pump. Fluid loops connect the catheter to the three port valve and the peristaltic pump, and between the first container, the filtration means and the second container. The fluid loops transport the cerebrospinal fluid from the subarachnoid compartment of the spinal canal through the three port valve into the first container through the filtration means returning the cerebrospinal fluid which has not been filtered back to the first container and the filtered cerebrospinal fluid to the second container. The filtered and treated fluid is then returned back through the three port valve into the spinal canal.

In another aspect of the present invention the filtration means includes a fiber cartridge for micro-filtration of the untreated cerebrospinal fluid by tangential flow filtration. The cartridge has a pore size of about 0.2 m$\mu$ and a membrane surface of about 450 cm$^2$. The flow of the untreated fluid is at right angles to the filtration direction. The direction of the flow is important for reducing membrane plugging and cake formation.

An additional embodiment of the monitoring device includes a pH electrode, a temperature probe, a flow meter, a bi-directional pressure transducer and a spectrophotometer. All of these devices are connected by an interface to the regulating means which comprises a computer and computer station including a monitor, a printer and a warning means. An interface connects the computer to the processing means. The interface allows for the exchange of data between the processing and regulating means so that the processing means can be controlled to regulate the flow, treatment, purification and monitoring of cerebrospinal fluid.

Further objects, features and advantages will be apparent from the following description of the preferred embodiment of the invention.

BRIEF DESCRIPTION OF THE DRAWINGS

So that the manner in which the above featured advantages and objects of the present invention will be more readily understood, a more particular description of the construction and operation may be had by reading the following specification and by references to the accompanying drawings forming a part thereof.

DETAILED DESCRIPTION OF PREFERRED EMBODIMENTS

In the description which follows like parts are marked throughout the specifications and drawings with the same referenced numerals. The drawings are not necessarily to scale and certain features of the invention may be exaggerated in scale or shown in schematic form in the interest of clarity and conciseness. It will be readily apparent to one skilled in the art that various substitutes and modifications may be made to the invention disclosed herein without departing from the scope and spirit of the invention.

Referring to FIGS. 1-4 we see the fluid exchange device 10. The processing means 13 includes a means for moving the cerebrospinal fluid 66 from the subarachnoid compartment of the spinal canal 33 through the processing means 13 and back to the subarachnoid compartment of the spinal canal 33. This means for moving has a reversible peristaltic pump 16. The peristaltic pump 16 provides a volume range from about 0.07 to 25 liters per hour and operates with a fluid pressure of not greater than about 30 PSI. In the preferred embodiment the peristaltic pump has three channels and six rollers for operation. The peristaltic pump 16 is connected to an interface which has an RS 232-C serial port for control of the pump direction which is clockwise or counter clockwise, the volume per minute flow and any necessary error messages.

Figure 3:
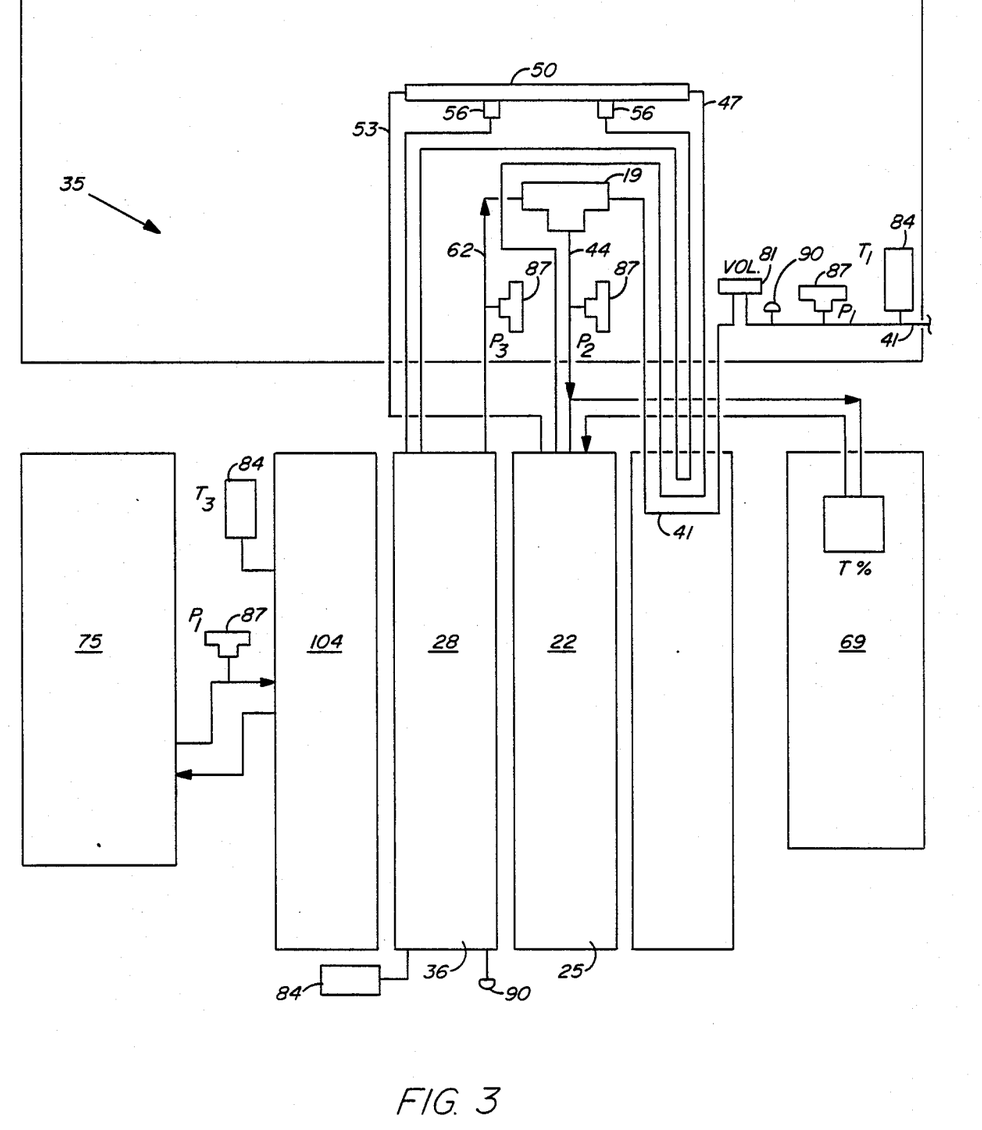
FIG. 3 is a schematic of the fluid loop used in the fluid exchange device.

In addition to the peristaltic pump 16 the processing unit also includes a three port valve means (FIG. 3). In the preferred embodiment the valve means is a 12 volt DC valve connected to the interface for synchronous control with the peristaltic pump 16. The three port valve 19 regulates the direction of flow of fluid between the different components of the apparatus. This direction is regulated such that fluid coming from the subarachnoid compartment of the spinal canal 33 enters the valve 19 and is directed to the first container 22 where the untreated cerebrospinal fluid 25 is stored. After the cerebrospinal fluid has been treated it is then stored in the second container 28. The valve 19 is also connected to the second container 28. For the return, treated cerebrospinal fluid 36 flows into the valve 19 and is then directed back into the subarachnoid compartment of the spinal canal 33.

The processing means 13 also includes fluid loops 35 which connect the collection means 38 and the processing means 10. The apparatus includes three fluid loops, a main fluid loop, an untreated fluid loop and a treated fluid loop.

The main fluid loop comprises a first tube 41 between the collection means 38 and the three port valve means 19. The tube 41 transports cerebrospinal fluid 66 from the subarachnoid compartment of the spinal canal 33 to the three port valve 19 and from the three port valve 19 back to the subarachnoid compartment of the spinal canal 33.

The untreated fluid loop comprises: a second tube 44 carrying untreated cerebrospinal fluid 25 from the three port valve means 19 to the first container 22; a third tube 47 carrying the untreated cerebrospinal fluid 25 from the first container 22 to the filtration means 50; and a fourth tube 53 carrying the cerebrospinal fluid 25 with impurities from the filtration means 50 back to the first container 22. In the preferred embodiment only part of the fluid which flows through the hollow fiber filtration means 50 is filtered. The fluid which has not been filtered and which washes the impurities out of the filtration means 50 is carried back to the first container 22.

The treated fluid loop includes a fifth tube 56 and a sixth tube 62. A plurality of these fifth tubes 56 can be connected to the filtration means 50 to carry the purified or filtered cerebrospinal fluid 36 flowing through the filter 50 back to the second container 28. The second container 28 stores the filtered cerebrospinal fluid 36 for reinjection into the spinal canal 33. The sixth tube 62 carries the purified or filtered cerebrospinal fluid 36 from the second container 28 to the three port valve means 19. The three port valve means can switch and direct the cerebrospinal fluid 36 into the main loop 41 for reinjection into the subarachnoid compartment of the spinal canal 33.

Thus, in summary, cerebrospinal fluid 66 flows through the main loop 41 as it passes from subarachnoid compartment of the spinal canal 33 into the three port valve 19 which directs the cerebrospinal fluid 66 into the untreated loop where the fluid is passed from the first container 22 to the filtration means 50. After filtration the fluid enters the treated loop and passes from the filtration means 50 to the second container 28 back to the three port valve 19 which directs the fluid into the main loop 41 where it re-enters the subarachnoid compartment of the spinal canal 33. It should be noted that the volume of the main loop tube 41 is quite small compared to the volume of cerebrospinal fluid 66 which is removed or cerebrospinal fluid 36 which is returned. In the preferred embodiment the total volume of the tube in the main fluid loop 41 is about 0.22 cc/foot whereas normally about 10 cc's of cerebrospinal fluid 66 are removed or reinjected during one cycle. Thus the greater volume which is removed or reinjected completely washes out or clears out the main fluid tube 41. Thus there is no recycling of untreated cerebrospinal fluid 25.

Figure 1:
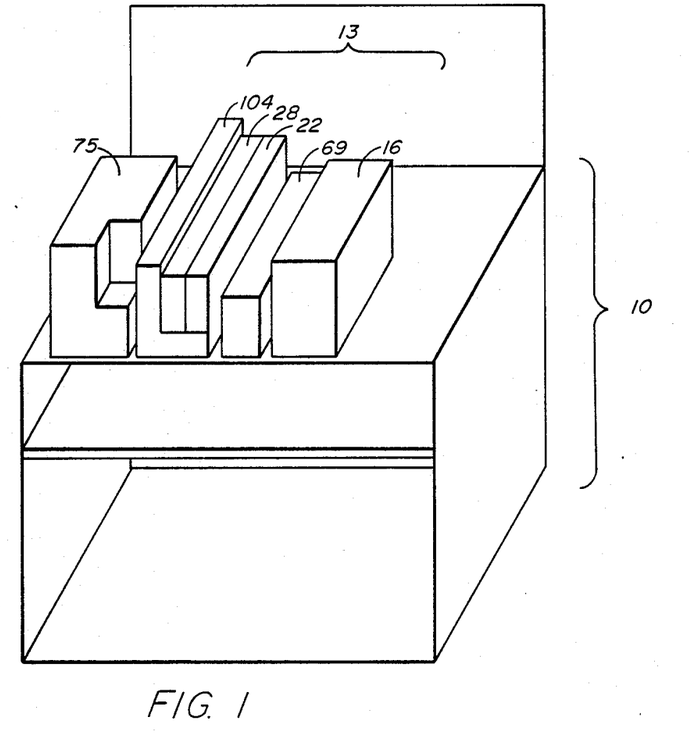
FIG. 1 is a perspective exploded elevational view of the processing unit of the fluid exchange device.

The fluid processing means can also include a spectrophotometer 69. In the preferred embodiment a digital model with a wave length range of 340 to 950 nm with 0-100% transmission and a RS 232-C serial input-/output interface connection is used. The spectrophotometer 69 can supply readings to the regulating means 72 so that the rate of fluid processed can be regulated and tested to see if blood and blood breakdown products, are being removed. Although all the fluid could flow through the spectrophotometer cell, the preferred system only samples a small portion about 0.25 to 1.5 cc of the about 10 cc sample.

The first container 22 is preferably a glass sterile container with a volume of about 3 to 7 liters. The first container 22 is cooled by the temperature regulating means 75. Untreated compatible cerebrospinal fluid 25 is stored in the first container 22.

A second container 28 is also included for the storage of the treated or filtered cerebrospinal fluid 36. The treated fluid container 28 is preferably a glass sterile container with a volume of about 3 to 7 liters. The treated cerebrospinal fluid 36 is cooled by the temperature regulation means 75, is pH adjusted and is filtered compatible cerebrospinal fluid.

The temperature regulating means 75 an be any device which regulates or can regulate the temperature of the apparatus. In the preferred embodiment the temperature regulating means 75 has a volume of about 3 liters, a temperature range of about $-15°$ to $50°$ C. with a regulation of about $\pm 0.1°$ C. Furthermore, it has a circulation flow of about 0 to 13 liters per minute and circulates fluid at about $8.5°$ to $12°$ C. A number of embodiments of the temperature regulating means 75 are available for use in the apparatus. In one specific embodiment the temperature regulating means is a container which holds the processing means 10 in a temperature regulated liquid. In another embodiment it is a refrigerator. In the preferred embodiment the coolant is circulated around the processing means 10 to regulate the cerebrospinal fluid. Alternatively the temperature regulation means 75 can have coils throughout the processing means 10, circulating coolant to regulate the temperature of the cerebrospinal fluid in the containers and tubes. In the preferred embodiment the cooling container has a glass receptacle 104 containing coolant for cooling the rest of the apparatus. Although no specific size is needed the device contains about 12 to 14 liters of coolant in the preferred embodiment. This is adequate to maintain the temperature during the operation of the fluid exchange device. The temperature regulating means 75 can also increase the temperature if necessary.

The filtration means 50 for filtering the cerebrospinal fluid can be any unit which removes contaminates from the cerebrospinal fluid 25. In the preferred embodiment a hollow filter using a fiber cartridge is employed. It is a self-contained unit used for the micro-filtration of the untreated cerebrospinal fluid 25. The cartridge has a pore size of from about 0.2 to 0.4 m$\mu$ and a membrane surface area of at least about 450 cm$^2$. In the preferred embodiment the pore size is about 0.2 m$\mu$ and the membrane surface area about 450 cm$^2$. Additionally, the hollow fiber cartridge uses a tangential flow filtration technique. The advantage of the tangential flow technique is that there is reduced membrane plugging the cake formation normally associated with the filtration of biological fluids. This reduction occurs because there is flow of untreated fluid at right angles to the direction of the filtration. The membranes are polysulfone, can be cleaned by auto cleaving at about $121°$ C. and can be reused several times.

A plurality of probes are included in the preferred embodiment for monitoring the processing of the cerebrospinal fluid. For example, a volume flow meter 81 is used in the first tube 41. In the preferred embodiment the flow meter 81 can measure about 0 to 49 millimeters per minute of primarily laminar fluid flow.

A variety of temperature probes 84 are used throughout the system. In the preferred embodiment a J-type thermocouple with a temperature range of about $-93°$ C. to $760°$ C. has been employed. A micro-volt signal is generated proportional to the temperature gradient between the measuring and reference junctions and recorded by the data interface.

Bi-directional pressure transducers 87 with a pressure range of about $-14$ to 10 PSI having a 1 to 6 volt output and requiring a 0 to 20 volt excitation voltage are used.

These pressure transducers 87 monitor the patient's cerebrospinal fluid pressure, positive system pressure, negative system pressure and refrigeration pump fluid pressure Additionally, pH probes 90 can be used in the system to monitor the pH of the cerebrospinal fluid. Selective pH measurement combination electrodes with a pH range of 0 to 13 and a temperature tolerance of 110° C., have been used. A plurality of pH electrodes can be attached to a pH transmitter which changes the pH signal into 4 to 20 mA output for interface with the regulating means. In the normal operation, the patient's arterial fluid pH and the cerebrospinal fluid pH, as measured in both the treated and untreated fluid, are used to monitor treatment.

Figure 2:
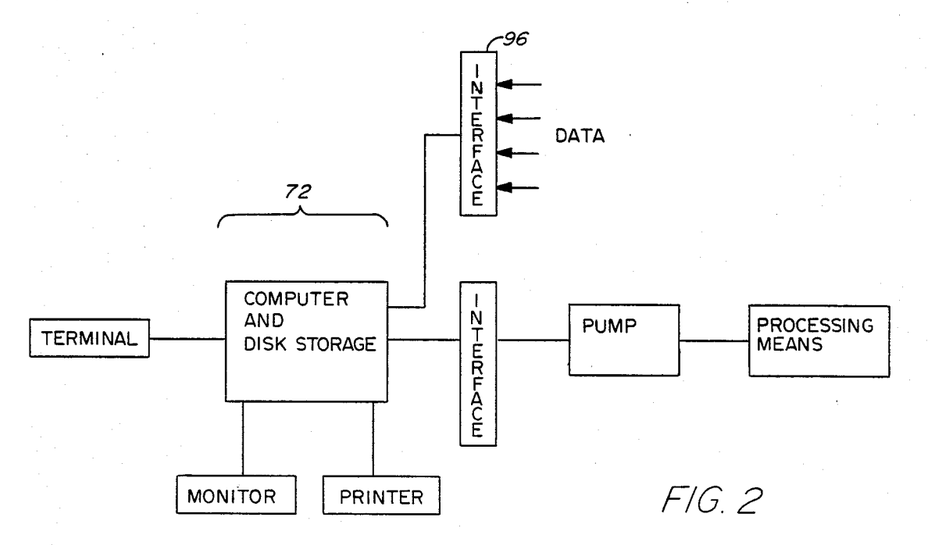
FIG. 2 is a schematic of the data processing unit.

All of the monitoring devices, the volume flow meter 81, temperature probes 84, pressure transducers 87 and pH meters 90 are connected to an interface 96 which is connected to the regulating means 72. The probes transmit electrical signals to the regulating means 72 which then interprets the signals and sends the results to a high resolution monitor and/or stores the data for later review. Using this information, a technician can regulate the flow, pH, temperature, pressure or other parameters in the system to maintain the appropriate conditions for the processing of the cerebrospinal fluid and the reintroduction of the cerebrospinal fluid into the subarachnoid compartment of the spinal canal. By monitoring the pH and regulating the addition of appropriate materials the pH in the cerebrospinal fluid can be maintained within physiological ranges.

Figure 4:
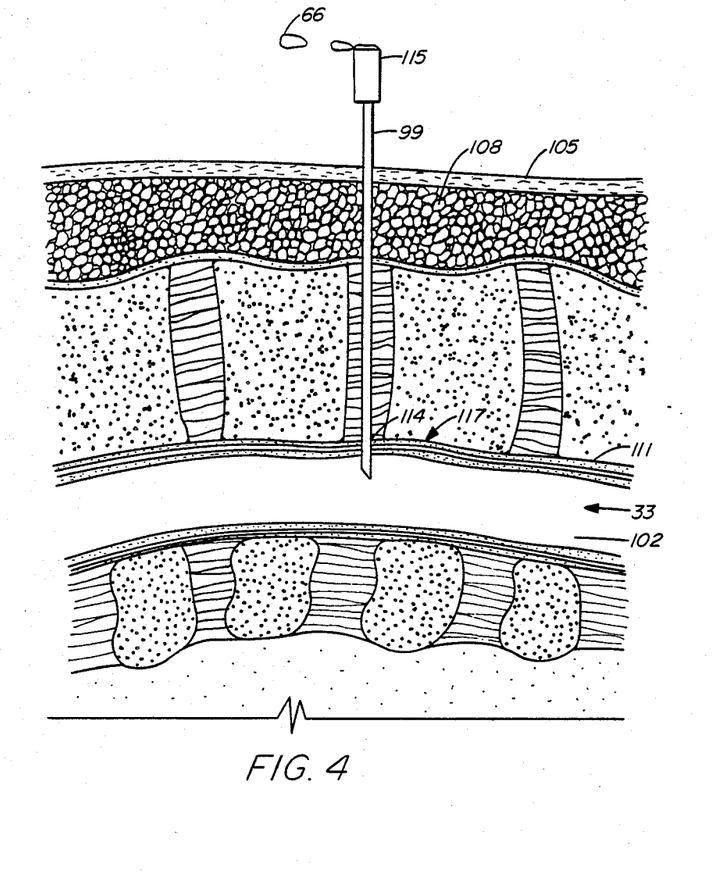
FIG. 4 is a perspective exploded elevational view showing the introduction of the cannula into the subarachnoid space.
Figure 5:
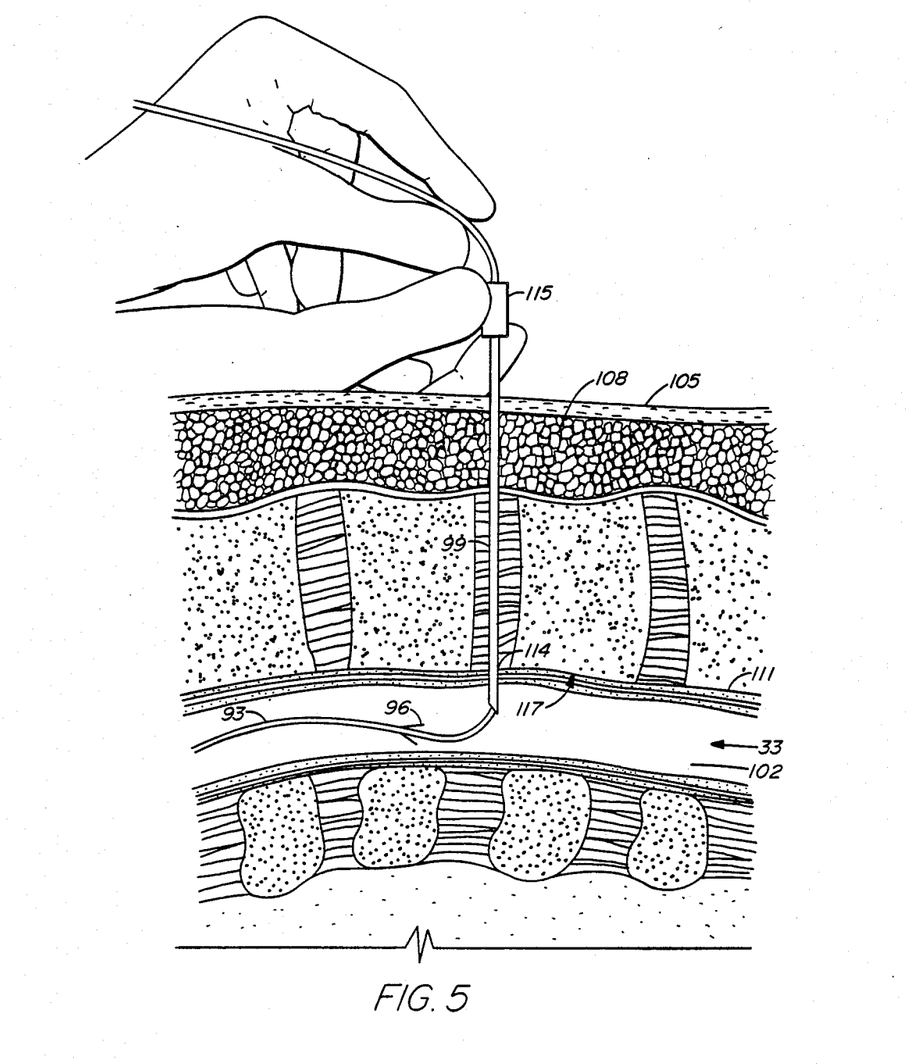
FIG. 5 is a elevational cross-sectional view showing the introduction of the silicon elastomer catheter into the subarachnoid space.

The fluid exchange device includes a collection means 38. The collection means 38 is used for obtaining cerebrospinal fluid 66 from the subarachnoid compartment of the spinal canal 33, as well as, returning cerebrospinal fluid 36 to the subarachnoid compartment of the spinal canal 33. The collection means 38 includes a cannula 99 which punctures the spinal canal providing a conduit for a catheter 93 which indwells in the subarachnoid compartment of the spinal canal 33. The catheter includes a flange 96 for retarding or inhibiting cerebrospinal fluid 66 leakage from the spinal canal 33. The collection means can be introduced into the spinal canal as seen in FIGS. 4 and 5. An extra-thin walled cannula 99 with an outside diameter of about 1.47 mm and an internal diameter of approximately 1.27 mm is introduced into the subarachnoid compartment of the spinal canal 33. In the preferred embodiment the cannula 99 is introduced into the subarachnoid compartment 33 and cerebrospinal fluid 66 is egressed. FIGS. 4 and 5 show in cross-section the skin 105, subcutaneous adipose tissue 108, and dura mater 111 that is penetrated by the cannula 99 as it moves into the subarachnoid compartment 102. After the cannula 99 is introduced the catheter 93 is passed through the cannula 99 and into the subarachnoid compartment 102 as seen in FIG. 5.

The catheter 93 is preferably made of a silicone elastomer. The preferred embodiment has an outside diameter of about 1.2 mm and internal diameter of about 0.97 mm. The flange 96 which is attached to the outside diameter of the cannula 99 is of sufficient size such that it blocks the puncture site 114 created in the spinal canal dura by the cannula 99. In the preferred embodiment, it is made of a silicone elastomer. When the flange 96 is engaged against the dural surface 117 of the spinal canal at the puncture site 114 it occludes the puncture opening.

Figure 6:
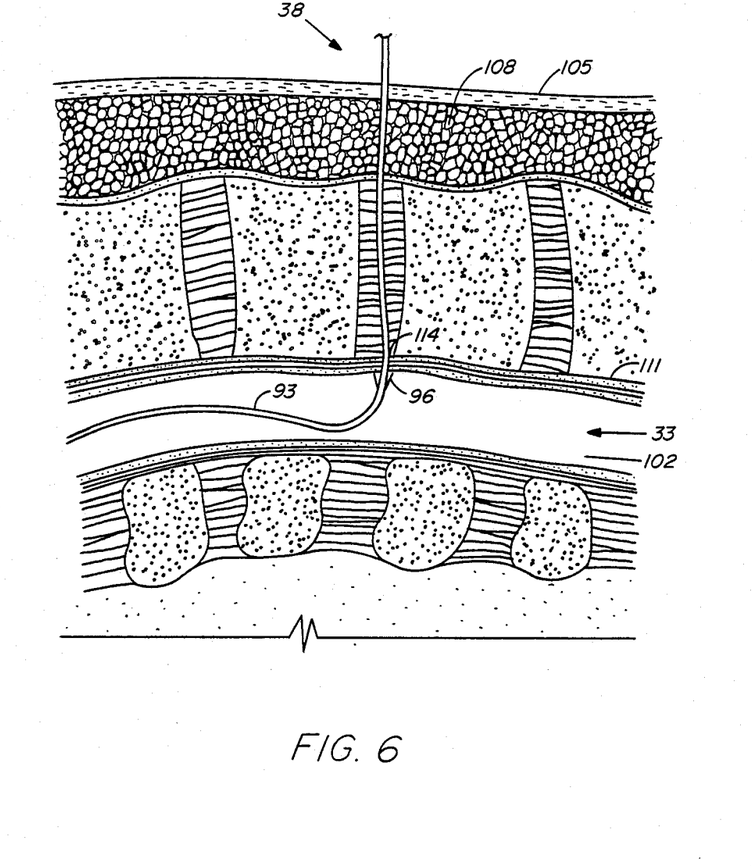
FIG. 6 is a cross-sectional view showing the placement of the silicon elastomer catheter in the subarachnoid space.

As seen in FIG. 5 the cannula 99 is secured at the hub 115 and the silicone elastomer catheter 93 with the attached flange 96 is threaded through the cannula and slides into the spinal canal subarachnoid compartment 102. After the silicone elastomer catheter 93 has been inserted into the subarachnoid compartment 102 the cannula 99 is removed. As seen in FIG. 6 the silicone elastomer catheter 93 is pulled back a sufficient distance allowing the flange 96 to contact the dural membrane 117 of the subarachnoid compartment 102. The flange 96 is of sufficient size to cover the puncture site 114 such that fluid 66 does not leak out of the subarachnoid compartment 102 other than through the silicone elastomer catheter 93.

Figure 7:
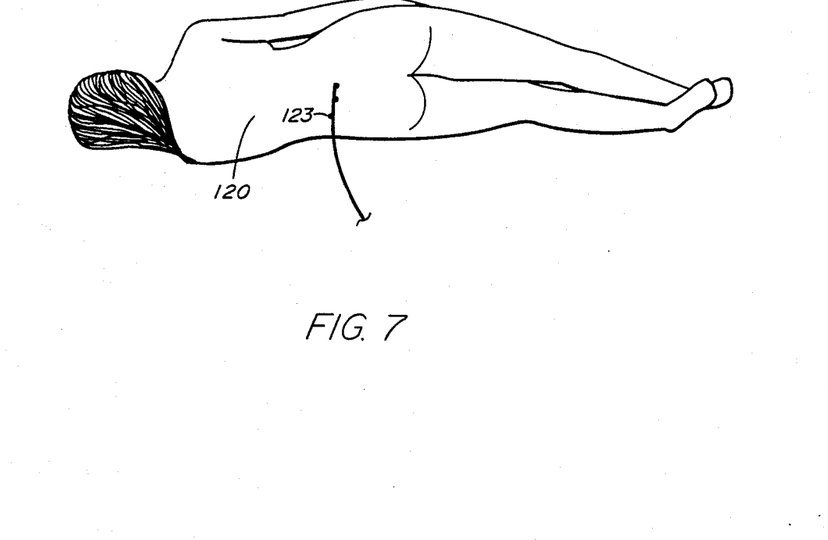
FIG. 7 is an elevational schematic view showing the patient with the subarachnoid catheter in situ.

After the placement of the indwelling catheter 93 the subject 120 is allowed to rest, FIG. 7. For example, in the case of humans the subject 120 will be allowed to rest on his side or back and skin tabs 123 are secured to the skin 105 to prevent the inadvertent displacement of the indwelling catheter 93 from the subarachnoid compartment 102. This device is also useful in the treatment of animals as well as humans. Thus, it can be used in the treatment of any vertebrate animals either for research or when sick.

The regulation means 72 is shown in schematic form in FIG. 2 and includes a computer for the collection of signals from the processing means 10 and for the sending of signals to regulate the processing means 10. In the preferred embodiment, an IBM compatible micro-computer is used. The preferred embodiment includes a 1.2 MEG ram and a 20 MEG hard disk capacity and one 360K floppy disk drive. A parallel port for the printer, two serial port RS 232-C connections, a 2400 baud modem, a pump valve interface, a data acquisition interface with 32 channels, a computer station for monitoring of the system by the technician, a warning means, a plurality of monitors and specific software for monitoring the subject The micro-processor IBM compatible computer receives signals from the pump 16, three port valve 19, temperature flow meter 81, pH probes 90, temperature probes 84, pressure probes 87 and spectrophotometer 69. The computer sends a signal to the pump 16 and three port valve 19 regulating the three port valve 19 settings and the direction, clockwise or counter clockwise, of the pump 16. This regulation is synchronous such that the fluid moves through the appropriate chamber at the appropriate time. The patient, the cerebrospinal fluid and the operation of this apparatus are monitored through the pump valve interface. The temperature, pH, pressure flow, and spectrophotometer readings are channeled through data acquisition interface data channels. Any dangerous or significant changes in the medical management of the patient is transmitted to the screen to alert the technician to the changes. Additionally, a warning means can be used. The warning means can be as simple as a beep coming from the computer terminal or a bell sounding an alarm to alert the technician that something is wrong with the system or that the patient's parameters have changed, requiring immediate attention. Alternatively, it could activate a voice synthesizer to call for assistance. The following table shows some of the parameters which are monitored in the preferred embodiment of the device.

| TABLE OF PARAMETERS | |
| --- | --- |
| Temperature | Body CSF temperature |
| | Treated CSF temperature |

-continued
TABLE OF PARAMETERS

| | |
|---|---|
| | Cooling reservoir temperature |
| | Body core temperature |
| Pressure | Body CSF pressure |
| | Pump negative pressure |
| | Pump positive pressure |
| | Cooling reservoir pressure |
| | Mean arterial pressure |
| | Cerebral perfusion pressure |
| Volume | Stroke volume |
| | Additive efferent volume |
| | Additive afferent volume |
| pH | Treated CSF pH |
| | Arterial pH |
| $pO_2$ | Arterial $O_2$ partial pressure |
| $pCO_2$ | Arterial $pCO_2$ partial pressure |

It can be seen that a plurality of temperature, pressure, pH, volume and biological parameters are monitored. All of these parameters are sampled by the computer during the continual monitoring of the patient. Whenever any parameter exceeds or drops below specific alarm ranges, the warning signal is sounded for immediate attention. Furthermore, alarm ranges can be established for the computer input of data to regulate the pressure of the pump, the selection of the three port valves, the addition of material to adjust the pH of the cerebrospinal fluid in the second container 28, and the adjustment of the temperature regulating means to control the temperature of the cerebrospinal fluid.

Figure 8:
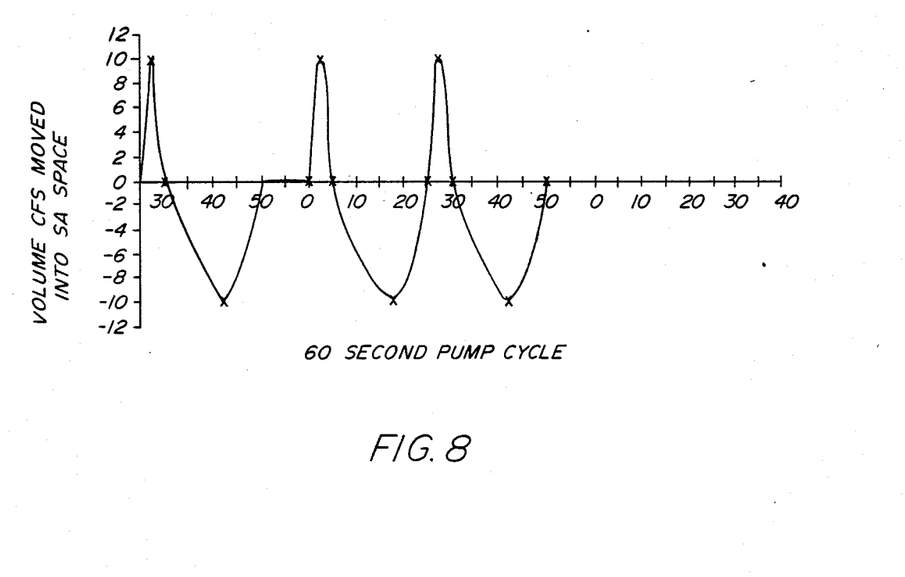
FIG. 8 is a schematic of the peristaltic pump cycle.

FIG. 8 shows the fluid exchange device pump cycle used for the operation of this apparatus in the preferred embodiment. At about 0 seconds and 25 seconds the pump is moving in a clockwise direction, in a positive pressure phase and the three port valve is switched by the pump valve interface to allow about 10 cc's of treated fluid to flow into the patient. This phase lasts about 5 seconds. During a negative pressure phase the pump reverses, the flow to a counter clockwise direction and the three port valve is changed to allow about 10 cc's of the patients cerebrospinal fluid to flow out of the cerebrospinal canal and into the untreated reservoir. This phase lasts about 20 seconds. The temperature, pressure, pH, volume and percent transmission of the cerebrospinal fluid is monitored. A stop phase of about 10 seconds allows accurate parameter sampling from the patient and the cerebrospinal fluid. It takes about one minute for every two cycles. The cycles include a positive pressure phase of about 5 seconds, a negative pressure phase of about 20 seconds, a positive pressure phase of about 5 seconds, a negative pressure phase of about 20 seconds and a stop phase of about 10 seconds.

The fluid flowing during the positive pressure phase from the processing device in the cerebrospinal fluid passes through the silicon elastomer catheter into the subarachnoid compartment of the spinal canal. The turbulence created in the subarachnoid compartment enhances the mixing of the treated fluid with the untreated fluid currently in the subarachnoid compartment. During the withdrawal of the cerebrospinal fluid, the mixed fluid rather than recycled treated fluid is withdrawn from the cavity. This is further enhanced by maintaining a very small volume in the main fluid loop tube compared to the actual volume of about 10 cc's of cerebrospinal fluid withdrawn or added. In the preferred embodiment this loop will have a volume of about 1.5 cc or less.

The present invention also includes a method for exchanging the cerebrospinal fluid of vertebrates. This method comprises the collection of cerebrospinal fluid from the vertebrate with the apparatus of the present invention. The collected cerebrospinal fluid is filtered and the physical and chemical parameters of both the cerebrospinal fluid and the body are monitored. The filtered cerebrospinal fluid then is returned to the vertebrate. The collecting, filtering, monitoring and returning of the cerebrospinal fluid is controlled by a regulation means within the apparatus. The method also includes the cooling of the fluid if necessary for the treatment. This apparatus can be used in a method for continuously removing blood, blood byproducts or drugs from cerebrospinal fluid. Because the apparatus can be connected to the vertebrate and left indwelling, cerebrospinal fluid can be continually removed, processed and returned to the vertebrate. Thus, the apparatus can be used for the continuously removing of blood and blood byproducts from the spinal fluid. During this continuing process the physical and chemical parameters of the cerebrospinal fluid can be monitored.

The fluid exchange apparatus can be used for the diagnosis, the management and/or the treatment of brain and spinal cord injuries and diseases. The injuries and diseases which can be treated for example include intra-cranial arterial vasospasm, subarachnoid hemorrhage, trauma to the brain and spinal cord and fetal intracranial hemorrhage. During the treatment, monitoring and diagnosis of many diseases it is important that the cerebrospinal fluid be cooled to facilitate the healing process. Thus the device can be operated in the cooling mode without filtering the cerebrospinal fluid if that is necessary.

One skilled in the art will readily recognize that the cerebrospinal fluid exchange device can be used to replace cerebrospinal fluid. In some instances rather than purify and reinject the cerebrospinal fluid it will be necessary to use artificial cerebrospinal fluid with corrected physical and/or chemical characteristics and to discard the removed cerebrospinal fluid. Alternatively the reinjected fluid may be a mixture of artificial and the removed cerebrospinal fluid.

One skilled in the art will readily appreciate the present invention is well adapted to carry out the objects and obtain the ends and advantages mentioned as well as those inherent therein. The methods, procedures, techniques, devices and apparatus described herein are presently representative of the preferred embodiments, are intended to be exemplary and are not intended as limitations on the scope. Changes therein and other uses will occur to those skilled in the art which are encompassed within the spirit of the invention or defined by the scope of the appended claims.

What is claimed is:

1. An apparatus for the exchange of cerebrospinal fluid comprising:
   a collection means for obtaining cerebrospinal fluid, wherein said collection means includes a catheter for indwelling in the subarachnoid compartment of a spinal canal, said catheter having a flange for retarding cerebrospinal fluid leakage from said spinal canal and a cannula for puncturing the spinal canal and providing a conduit for said catheter;
   a processing means, attached to said collection means, for monitoring the exchange of cerebrospinal fluid; and a regulation means for controlling the processing means and regulating the exchange of cerebrospinal fluid; and an interface for connecting the processing means to the regulation means.

2. The apparatus of claim 1, wherein, more particularly, said catheter and said flange are silicone elastomers and said flange is attached to the external surface of said catheter and engages the spinal canal at the puncture site.

3. The apparatus of claim 2, wherein, more particularly, said catheter has an outside diameter of about 1.22 mm and an internal diameter of about 0.97 mm.

4. The apparatus of claim 1 wherein, more particularly, the processing means comprises:

a first container for holding untreated cerebrospinal fluid;

a filtration means for removing particulate matter from said untreated cerebrospinal fluid;

a second container for storing filtered cerebrospinal fluid;

a means for moving said cerebrospinal fluid, wherein said means for moving removes fluid from said spinal canal, passing said cerebrospinal fluid through said first container, said filtration means, said second container and back into said spinal canal;

a temperature regulating means for controlling the temperature of said cerebrospinal fluid; and a means for monitoring physical and chemical characteristics of said cerebrospinal fluid.

5. The apparatus of claim 4, wherein, more particularly, the means for moving includes:

a peristaltic pump, wherein said pump is reversible, has a volume range of about 0.07 to 25 liters per hour, an operating pressure of less than about 30 PSI and is attached to said regulating means through said interface;

a three port valve means connected to said regulating means through said interface for synchronous control with said pump; and a fluid loop connecting said collection means and said processing means;

wherein said fluid loops transport cerebrospinal fluid from said spinal canal through said processing means and back to said spinal canal.

6. The apparatus of claim 5, wherein, more particularly, the fluid loop includes:

a main fluid loop comprising a first tube between said collection means and said three port valve means;

an untreated fluid loop comprising a second tube for carrying said cerebrospinal fluid from said three port valve means to said first container, a third tube for carrying said cerebrospinal fluid from said first container to said filtration means, a fourth tube for carrying unfiltered cerebrospinal fluid from said filtration means back to said first container;

a treated fluid loop comprising a fifth tube for carrying filtered cerebrospinal fluid from said filtration means to said second container and a sixth tube for carrying filtered cerebrospinal fluid from said second container to said three port valve means;

wherein said loops pass through said temperature regulating means and said reversible peristaltic pump and wherein said regulating means controls the direction of flow of said cerebrospinal fluid by regulating the direction of said peristaltic pump and the open ports of said three port valve means such that cerebrospinal fluid flows from said spinal canal through the main fluid loop, the untreated fluid loop, the treated fluid loop and back through the main fluid loop to said spinal canal.

7. The apparatus of claim 4, wherein, more particularly, the filtration means includes a hollow fiber cartridge for micro-filtration of said cerebrospinal fluid by tangential flow filtration, said cartridge having a pore size of about 0.2 m, a membrane surface area of at least about 450 $cm^2$, wherein said cartridge is configured to allow said fluid flows at right angles through wall of said cartridge.

8. The apparatus of claim 4, wherein, said means for monitoring includes:

a pH electrode for measuring the pH of said cerebrospinal fluid;

a temperature probe for measuring the temperature of said cerebrospinal fluid;

a flow meter for measuring the volume of said cerebrospinal fluid flowing between the three port valve means and said spinal canal;

bi-directional pressure transducers for monitoring cerebrospinal fluid pressure; and a spectrophotometer for monitoring spectrophotometric transmittance in the cerebrospinal fluid, wherein said pH electrode, temperature probe, flow meter, pressure transducer and spectrophotometer are connected to said regulating means through said interface.

9. The apparatus of claim 1, wherein, more particularly, the regulation means comprises:

a computer; and a technician station connected to said computer for providing results, including a monitor, a printer and a warning means.

10. The apparatus of claim 9, wherein, more particularly the computer is an IBM compatible micro-computer.

11. An apparatus for the exchange of cerebrospinal fluid comprising:

an extra-thin walled stainless steel cannula for puncturing a spinal canal, a said cannula having an outside diameter of about 1.47 mm and an internal diameter of about 1.25 mm;

a silicone elastomer catheter for inserting into said cannula and for indwelling in the subarachnoid compartment of said spinal canal, said catheter having an outside diameter of about 1.22 mm and an inside diameter of about 0.97 mm;

a flange for retarding leakage of said cerebrospinal fluid from said spinal canal by engaging said spinal canal at the puncture site, said flange being attached to the external surface of said catheter;

a first container for holding cerebrospinal fluid;

a fiber cartridge for micro-filtration of cerebrospinal fluid by tangential flow filtration, said fiber cartridge having a pore size of about 0.2 m$\mu$ and a membrane surface area of at least about 450 $cm^2$;

a second container for storing filtered cerebrospinal fluid;

a means for moving said cerebrospinal fluid, including, a reversible peristaltic pump with a volume range of about 0.07 to 25 liters per hour and an operating pressure of less than about 30 PSI, a three port valve means for regulating the direction of flow of said cerebrospinal fluid, and a fluid loop for carrying said cerebrospinal fluid, wherein said fluid loop connects said catheter to said three port valve means; said three port valve means to said first container and said second container; and said filtration device to said first container and said second container; and a temperature probe for measuring the temperature of said cerebrospinal fluid;

a temperature regulating means connect to said temperature probe for controlling the temperature of said cerebrospinal fluid;

a flow meter for measuring the volume of cerebrospinal fluid;

bi-directional pressure transducers for monitoring cerebrospinal fluid pressure;

a spectrophotometer for monitoring transmittance of the cerebrospinal fluid;

a computer for regulating the exchange of said cerebrospinal fluid and for controlling the treatment and flow of said cerebrospinal fluid;

a computer station connected to said computer for displaying results, said computer station includes a monitor, a printer and a warning means; and an interface for connecting said computer to said peristaltic pump, said three port valve means, said pH electrode, said temperature probe, said flow meter, said pressure transducers, said spectrophometer and said temperature regulating means.

12. The method of exchanging cerebrospinal fluid in a vertebrate comprising the steps of:
collecting cerebrospinal fluid from said vertebrate;
treating the collected cerebrospinal fluid;
monitoring the physical and chemical parameters of the cerebrospinal fluid;
returning the treated cerebrospinal fluid to said vertebrate; and
regulating the collecting, treating, monitoring and returning of said cerebrospinal fluid.

13. The method of claim 12, comprising the further step of cooling the cerebrospinal fluid.

14. A method for continuously removing blood, blood byproducts and other impurities from cerebrospinal fluid comprising the steps of:
collecting said cerebrospinal fluid with a catheter inserted into the subarachnoid compartment, said catheter having an outside diameter of about 1.22 mm and an internal diameter of about 0.97 mm;
micro-filtering said cerebrospinal fluid with a hollow fiber cartridge and tangential flow filtration; monitoring physical and chemical parameters of said cerebrospinal fluid with a monitoring means including means for measuring pH, pressure, temperature, volume and percent transmission;
returning said filtered cerebrospinal fluid to said vertebrate; and
regulating the collecting, filtering, monitoring and returning of the cerebrospinal fluid with a computer interfaced to said collecting, filtering and monitoring means, wherein said computer receives signals from the monitoring means and sends signals to the collecting filtering and returning means.

15. The method of claim 14 for the diagnosis, management and treatment of brain and spinal cord injuries and diseases.

16. The method of claim 15, wherein said injuries and diseases are selected from the group consisting of intracranial arterial vasospasm, subarachnoid hemorrhage, trauma and fetal intracranial hemorrhage.

17. The method of treating brain and spinal cord injury including the steps of:
continuously collecting cerebrospinal fluid from an injured vertebrate;
cooling said cerebrospinal fluid;
filtering said cerebrospinal fluid;
monitoring physical and chemical parameters of said cerebrospinal fluid; and
returning treated or artificial cerebrospinal fluid to said vertebrate.

* * * * *